US012364490B2

(12) United States Patent
Thibodeau et al.

(10) Patent No.: US 12,364,490 B2
(45) Date of Patent: Jul. 22, 2025

(54) DRILL GUIDE ASSEMBLY

(71) Applicant: Conmed Corporation, Utica, NY (US)

(72) Inventors: Robert A Thibodeau, Saint Petersburg, FL (US); Gregory A Alfonso, Seffner, FL (US); Matthew C Summitt, Palm Harbor, FL (US); Joaquim Casanas, Barcelona (ES)

(73) Assignee: Conmed Corporation, Utica, NY (US)

( * ) Notice: Subject to any disclaimer, the term of this patent is extended or adjusted under 35 U.S.C. 154(b) by 937 days.

(21) Appl. No.: 17/284,502

(22) PCT Filed: Jun. 12, 2019

(86) PCT No.: PCT/US2019/036660
§ 371 (c)(1),
(2) Date: Apr. 12, 2021

(87) PCT Pub. No.: WO2020/076376
PCT Pub. Date: Apr. 16, 2020

(65) Prior Publication Data
US 2021/0386438 A1     Dec. 16, 2021

Related U.S. Application Data

(60) Provisional application No. 62/744,686, filed on Oct. 12, 2018.

(51) Int. Cl.
*A61B 17/17* (2006.01)
*A61B 17/00* (2006.01)

(52) U.S. Cl.
CPC ............ *A61B 17/1782* (2016.11); *A61B 2017/00438* (2013.01)

(58) Field of Classification Search
CPC .......................................... A61B 17/17–1796
See application file for complete search history.

(56) References Cited

U.S. PATENT DOCUMENTS 4,739,751 A * 4/1988 Sapega ............ A61B 17/1764
606/88
5,234,434 A * 8/1993 Goble ............. A61B 17/1714
606/88
(Continued)

FOREIGN PATENT DOCUMENTS

| JP | 2002102236 | 4/2002 |
| WO | WO2017048826 A1 | 3/2017 |
| WO | 2017187436 A1 | 11/2017 |

OTHER PUBLICATIONS

International Search Report Form PCT/ISA/220, International Application No. PCT/US2019/036660, pp. 1-13, Dated Sep. 20, 2019.
(Continued)

*Primary Examiner* — Matthew J Lawson
(74) *Attorney, Agent, or Firm* — Bond, Schoeneck & King, PLLC; Frederick J. M. Price

(57) ABSTRACT

A drill guide for controlling the first metacarpal while maintaining the proper trajectory of the drill. The drill guide includes a guide rail having an elongated shaft and a guide body with an aperture extending therethrough. The aperture is configured to receive the elongated shaft of the guide rail. The drill guide also includes a distal ring connected to the elongated shaft. A spike and a hook are both attached to the distal ring and extend therefrom. The hook and the spike extend from opposing positions along the distal ring. A trigger end of the guide body has a trigger that, when actuated, allows the guide body to slide along the guide rail in a proximal direction. A drilling end of the guide body has a rotatable drill bullet extending distally therefrom. The drill bullet includes a pair of arms lined with teeth for engaging the first metacarpal.

20 Claims, 8 Drawing Sheets

(56) References Cited

U.S. PATENT DOCUMENTS

| | | | |
|---|---|---|---|
| 5,312,412 A | 5/1994 | Whipple | |
| 5,613,971 A | 3/1997 | Lower et al. | |
| 6,120,511 A * | 9/2000 | Chan | A61B 17/1637 606/179 |
| 6,210,415 B1 | 4/2001 | Bester | |
| 6,342,056 B1 | 1/2002 | Mac-Thiong et al. | |
| 6,755,838 B2 | 6/2004 | Trnka | |
| 7,815,646 B2 * | 10/2010 | Hart | A61B 17/1714 606/96 |
| 8,313,492 B2 | 11/2012 | Wong et al. | |
| 8,403,939 B2 | 3/2013 | Kortenbach | |
| 8,409,225 B2 | 4/2013 | Bull et al. | |
| 8,617,168 B2 | 12/2013 | Bourque et al. | |
| 8,764,763 B2 | 7/2014 | Wong et al. | |
| 8,795,286 B2 | 8/2014 | Sand et al. | |
| 8,956,278 B2 | 2/2015 | Torrie et al. | |
| 9,149,285 B2 | 10/2015 | Bourque et al. | |
| 9,463,034 B2 | 10/2016 | Wong et al. | |
| 9,848,895 B1 | 12/2017 | Alvarado et al. | |
| 9,936,994 B2 | 4/2018 | Smith et al. | |
| 10,010,333 B2 | 7/2018 | Ardito et al. | |
| 10,022,138 B2 | 7/2018 | Wong et al. | |
| 10,357,260 B2 | 7/2019 | Triplett et al. | |
| 10,702,290 B2 | 7/2020 | Triplett et al. | |
| 10,849,670 B2 | 12/2020 | Santrock et al. | |
| 2002/0183759 A1 | 12/2002 | Green et al. | |
| 2006/0195108 A1 | 8/2006 | Fox | |
| 2006/0195116 A1 | 8/2006 | Fox | |
| 2007/0162039 A1 * | 7/2007 | Wozencroft | A61B 17/15 606/89 |
| 2007/0276400 A1 | 11/2007 | Moore et al. | |
| 2012/0123417 A1 | 5/2012 | Smith | |
| 2012/0136357 A1 | 5/2012 | Torrie et al. | |
| 2014/0214095 A1 | 7/2014 | Rosenwasser et al. | |
| 2014/0228848 A1 | 8/2014 | Torrie et al. | |
| 2014/0277450 A1 | 9/2014 | Warburton | |
| 2016/0074049 A1 | 3/2016 | Russell et al. | |
| 2016/0089160 A1 * | 3/2016 | Ardito | A61B 17/17 606/96 |
| 2017/0119406 A1 * | 5/2017 | Triplett | A61B 17/86 |
| 2017/0245884 A1 | 8/2017 | Torrie | |
| 2018/0110542 A1 | 4/2018 | Devasconcellos | |
| 2018/0333161 A1 | 11/2018 | Ardito et al. | |
| 2019/0167281 A1 * | 6/2019 | Zilberman | A61B 17/1714 |

OTHER PUBLICATIONS

JP Office Action, App. No. 2021-519585, dated Apr. 1, 2022, pp. 1-8.

Examination Report No. 1, Application No. 2022205206, pp. 1-8, dated Aug. 21, 2023.

Translated Japanese Office Action, Application No. 2023-046122, dated Feb. 20, 2024, pp. 1-8.

"Translated KR Office Action, Application No. 10-2023-7031567, dated May 2, 2024, entire document".

"CA Office Action, application No. 311181, dated Jun. 6, 2024, entire document".

* cited by examiner

DRILL GUIDE ASSEMBLY

CROSS-REFERENCES TO RELATED APPLICATIONS

This application is a national stage application under 35 U.S.C. 371 based on international patent application PCT/US19/36660 filed on Dec. 6, 2019, which claims priority to U.S. Provisional Patent Application Ser. No. 62/744,686 filed on Oct. 12, 2018 and entitled "CMC Drill Guide," the entireties of which are incorporated herein by reference.

BACKGROUND OF THE INVENTION

1. Field of the Invention

The present invention is directed generally to a surgical system and, more particularly, to a drill guide to maintain particular positioning of bones in the thumb while maintaining the proper trajectory of a drill/drill bit.

2. Description of Related Art

The carpometacarpal (CMC) joint is located at the base of the thumb and is responsible for providing a wide range of motion to the thumb. A CMC suspension is a procedure for repairing damage at the CMC joint. During the CMC suspension procedure, a surgeon will drill through the base of the first metacarpal and the proximal end of the second metacarpal. By using a drill guide, the surgeons can drill all the way through both the first and second metacarpals in one step. However, the first metacarpal is loose due to the removal of the trapezium before drilling, making the process of drilling at the desired location difficult. Further, when drilling in smaller bones, such as the first metacarpal, accuracy is critical.

Therefore, there is a need for a device configured to control the first metacarpal while maintaining the proper trajectory of the drill/drill bit.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a drill guide for controlling the first metacarpal while maintaining the proper trajectory of a drill/drill bit. According to one aspect, the present invention is a drill guide. The drill guide includes a guide rail having an elongated shaft and a guide body with an aperture extending therethrough. The aperture is configured to receive the elongated shaft of the guide rail. The guide body of the drill guide also includes a trigger end. The trigger end has a locking mechanism that is movable between an unlocked position and a locked position. In the unlocked position, the guide body is slidable along the guide rail in a proximal direction.

According to another embodiment, the drill guide includes a guide rail having an elongated shaft and a guide body with an aperture extending therethrough. The aperture is configured to receive the elongated shaft of the guide rail. The guide body also includes a drilling end with an aperture, creating an inner volume extending therethrough. The inner volume is configured to receive a drill bullet (which can be configured to fit a drill bit therein) therein. The drill bullet is rotatable within the inner volume of the drilling end of the guide body.

According to an additional embodiment, the drill guide includes a guide rail having an elongated shaft extending along a first central longitudinal axis and a guide body with an aperture extending therethrough. The aperture is configured to receive the elongated shaft of the guide rail. The drill guide also includes a distal ring connected to the elongated shaft. A spike is attached to the distal ring and extends therefrom. A hook is also attached to the distal ring. The hook extends from the ring such that the hook and the spike extend from opposing positions along the distal ring.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
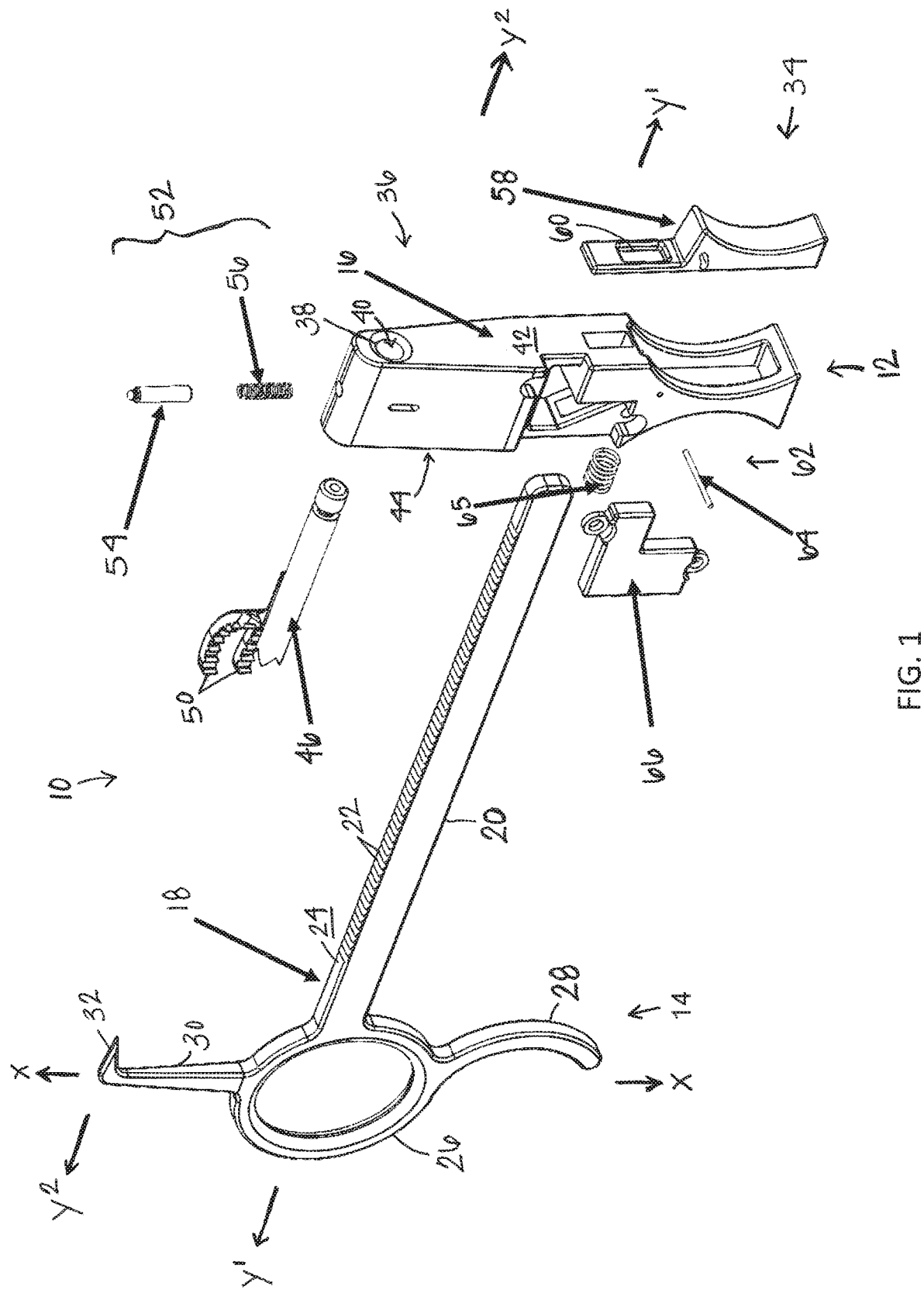
FIG. 1 is an exploded perspective view schematic representation of a drill guide, according to an embodiment.

Referring now to the figures, wherein like reference numerals refer to like parts throughout, FIG. 1 shows an exploded perspective view schematic representation of a drill guide 10, according to an embodiment. The drill guide 10 comprises a proximal end 12 and a distal end 14. At the proximal end 12, the drill guide 10 includes a guide body 16. The guide body 16 is configured to slide along a guide rail 18, which extends to the distal end 14.

As shown in FIG. 1, the guide rail 18 has an elongated shaft 20 extending toward the proximal end 12 of the drill guide 10. The guide rail 18 extends along a central longitudinal $y^1$-$y^1$ axis. The guide rail 18 comprises a plurality of ridges 22 extending along at least a portion of a surface 24 of the guide rail 18. The guide rail 18 can have a distal ring 26 connected to the elongated shaft 20. The distal ring 26 has a hook 28 extending therefrom. In the depicted embodiment, the hook 28 is curved in the distal direction (but can curve in the proximal direction), extending substantially along a lateral x-x axis. In the depicted embodiment, the ring 26 is substantially planar along the lateral x-x axis.

Still referring to FIG. 1, the guide rail 18 additionally includes a spike 30 extending from the ring 26. In the depicted embodiment, the spike 30 extends substantially along the lateral x-x axis. As shown in FIG. 1, the spike 30 extends from the ring 26 in a direction opposing the hook 28 (but could extend in the same direction as the hook 28). In the depicted embodiment, the lateral x-x axis is substantially perpendicular to the central longitudinal $y^1$-$y^1$ axis. FIG. 1 also shows that the spike 30 includes a sharp tip 32 extending in the proximal direction.

At the proximal end 12 of the drill guide 10, the guide body 16 includes a trigger end 34 and a drilling end 36. The drilling end 36 of the guide body 16 includes an aperture 38 defining an inner volume 40 extending from a proximal surface 42 of the guide body 16 to a distal surface 44 of the guide body 16. In the depicted embodiment, the inner volume 40 extends along a central longitudinal $y^2$-$y^2$ axis, which extending substantially parallel to the central longitudinal $y^1$-$y^1$ axis. In the depicted embodiment, the sharp tip 32 of the spike 30 also extends along the central longitudinal $y^2$-$y^2$ axis such that the sharp tip 32 is substantially aligned with the aperture 38 and/or inner volume 40 of the drilling end 36 of the guide body 16.

The inner volume 40 of the drilling end 36 of the guide body 16 is configured to receive a drill bullet 46. The drill bullet 46 includes a shaft 48 extending proximally along the central longitudinal $y^2$-$y^2$ axis and a pair of arms 50 extending distally from the shaft 48. The drilling end 36 of the guide body 16 can also include a locking mechanism 52 that maintains the drill bullet 46 in the desired position. In the depicted embodiment, the locking mechanism 52 includes a slug 54 (e.g., post) and a spring 56, as described in detail below.

Still referring to FIG. 1, the trigger end 34 of the guide body 16 includes a trigger 58 with an aperture 60 extending therethrough, which is configured to slidably receive the guide rail 18. The trigger 58 is connected to a locking mechanism 62 for locking the position of the guide body 16 along the guide rail 18. In the depicted embodiment, the locking mechanism 62 includes a spring 65 that maintains pressure on the trigger 58 and a trigger pin 64 that allows the trigger 58 to toggle between an unlocked position and a locked position, as described in detail below. As shown, the locking mechanism 62 is maintained within the guide body 16 with a cover plate 66.

Figure 2:
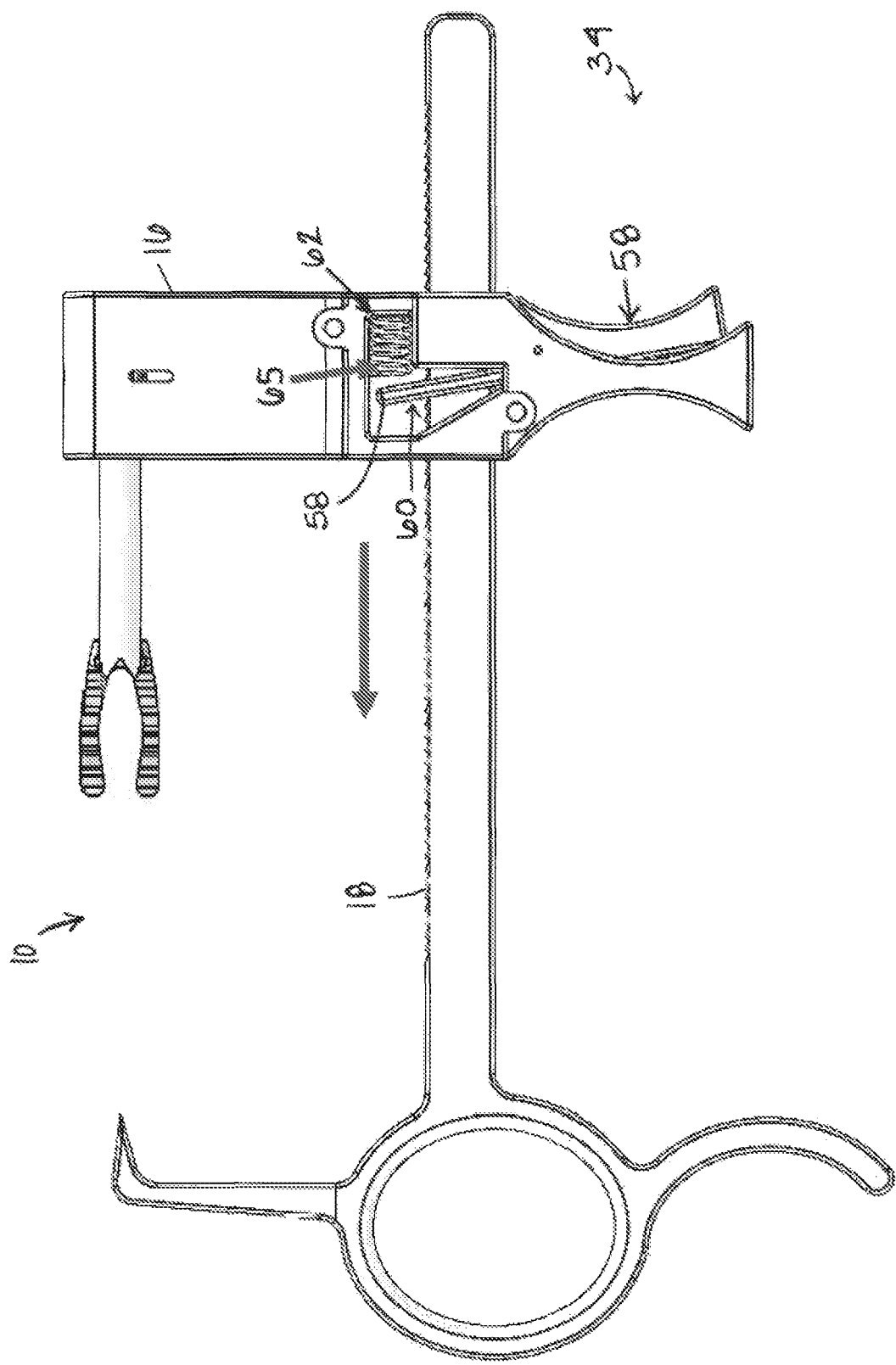
FIG. 2 is a side view schematic representation of the drill guide in a locked position, according to an embodiment.
Figure 3:
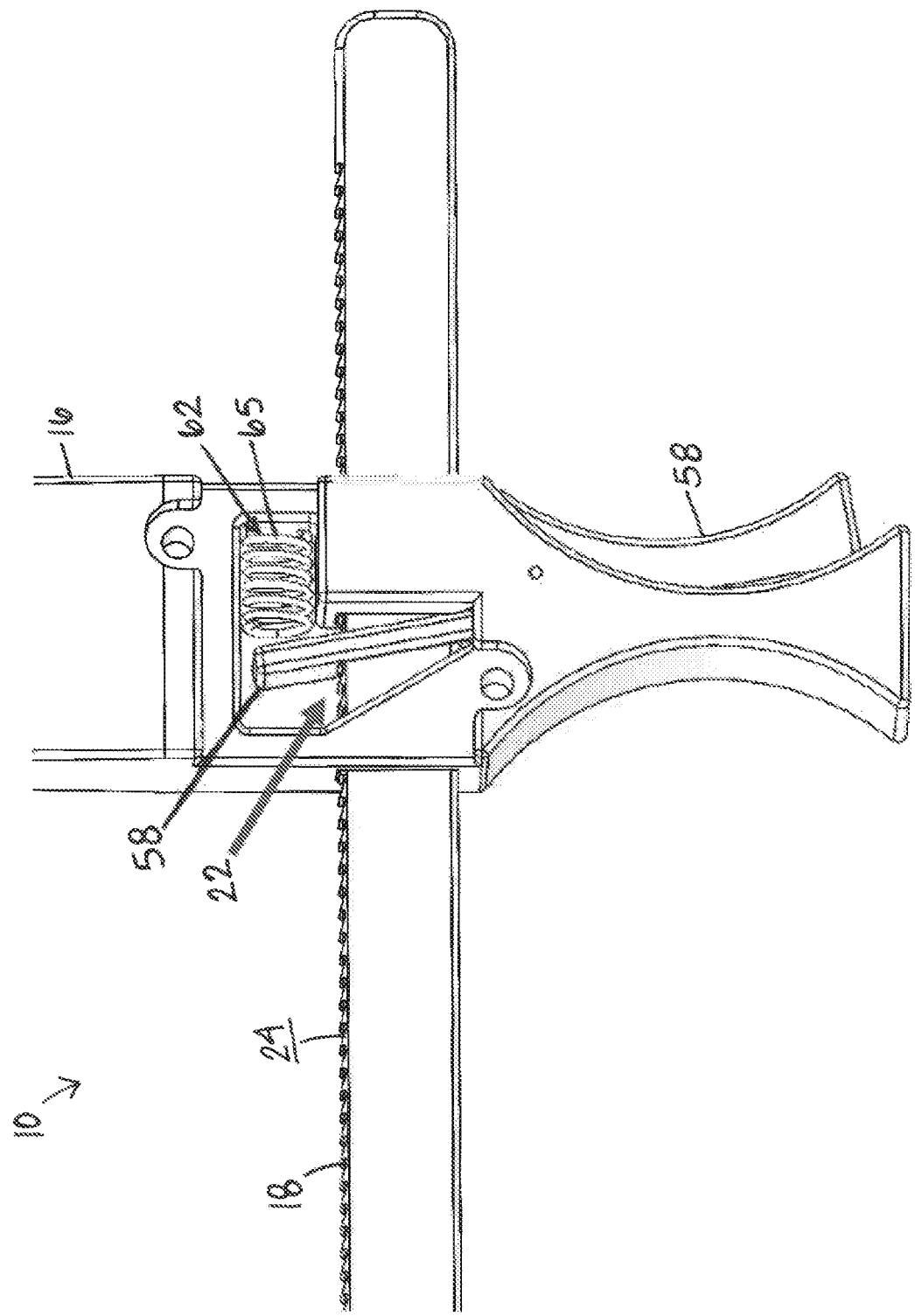
FIG. 3 is a close-up side view schematic representation of the trigger in the locked position, according to an embodiment.
Figure 4:
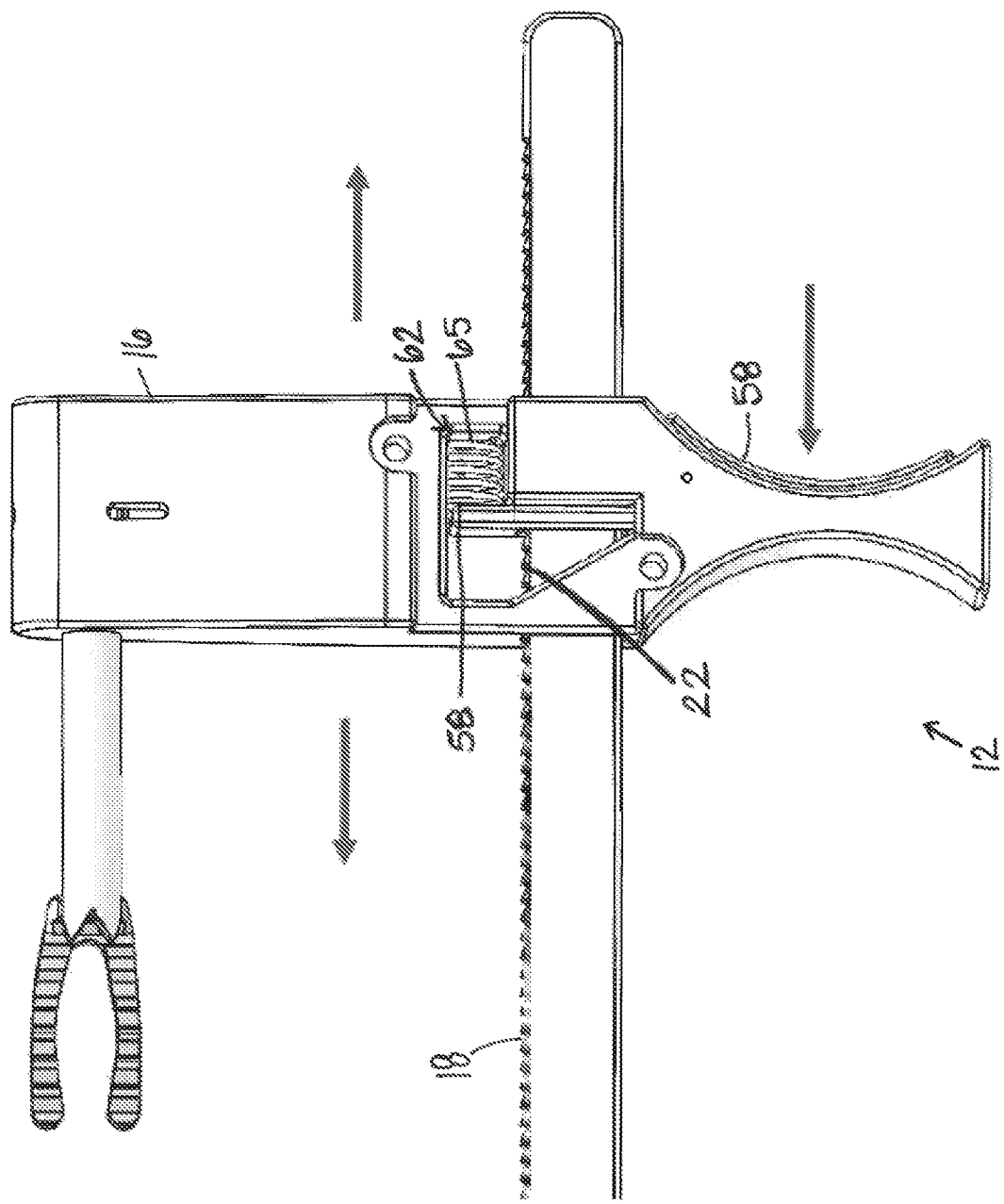
FIG. 4 is a side view schematic representation of the proximal end of the drill guide in an unlocked position, according to an embodiment.

Turning now to FIGS. 2-4, there are shown various views schematic representations of the trigger end 34 (with the cover plate 66 removed) of the guide body 16, according to an embodiment. FIG. 2 shows a side view of the drill guide 10 in the locked position. As stated above, the trigger end 34 of the guide body 16 includes the trigger 58 with the aperture 60 configured to receive the guide rail 18 therethrough. In the locked position, the locking mechanism 62 is biased such that the trigger 58 is spaced from (or at least not actively engaged with) the spring 65 of the locking mechanism 62.

In the locked position (FIGS. 2-3), the guide body 16 can slide distally along the guide rail 18. However, the guide body 16 cannot slide in the proximal direction. As shown in FIG. 3, the plurality of ridges 22 extending along the surface 24 of the guide rail 18 prevent the trigger 58 (and consequently, the guide body 16) from moving in the proximal direction when the trigger 58 is in the locked position. As shown in FIG. 3, in its relaxed, natural (locked) position, the trigger 58 catches on the ridges 22 when the guide body 16 is pulled/pushed in the proximal direction along the guide rail 18.

FIG. 4 shows a side view of the proximal end 12 (with the cover plate 66 removed) of the drill guide 10 in the unlocked position. To move the drill guide 10 from the locked position (FIGS. 2-3) to the unlocked position (FIG. 4), pressure is applied to the trigger 58. When the surgeon squeezes the trigger 58, the trigger 58 is rotated away from the plurality of ridges 22 and against the spring 65 of the locking mechanism 62. As the trigger 58 is clear from the ridges 22, the guide body 16 can be pulled/moved in the proximal direction without catching on the ridges 22. Thus, in in the unlocked position, the guide body 16 can slide proximally and distally along the guide rail 18 and in the locked position, the guide body 16 can only slide distally along the guide rail 18.

Figure 5:
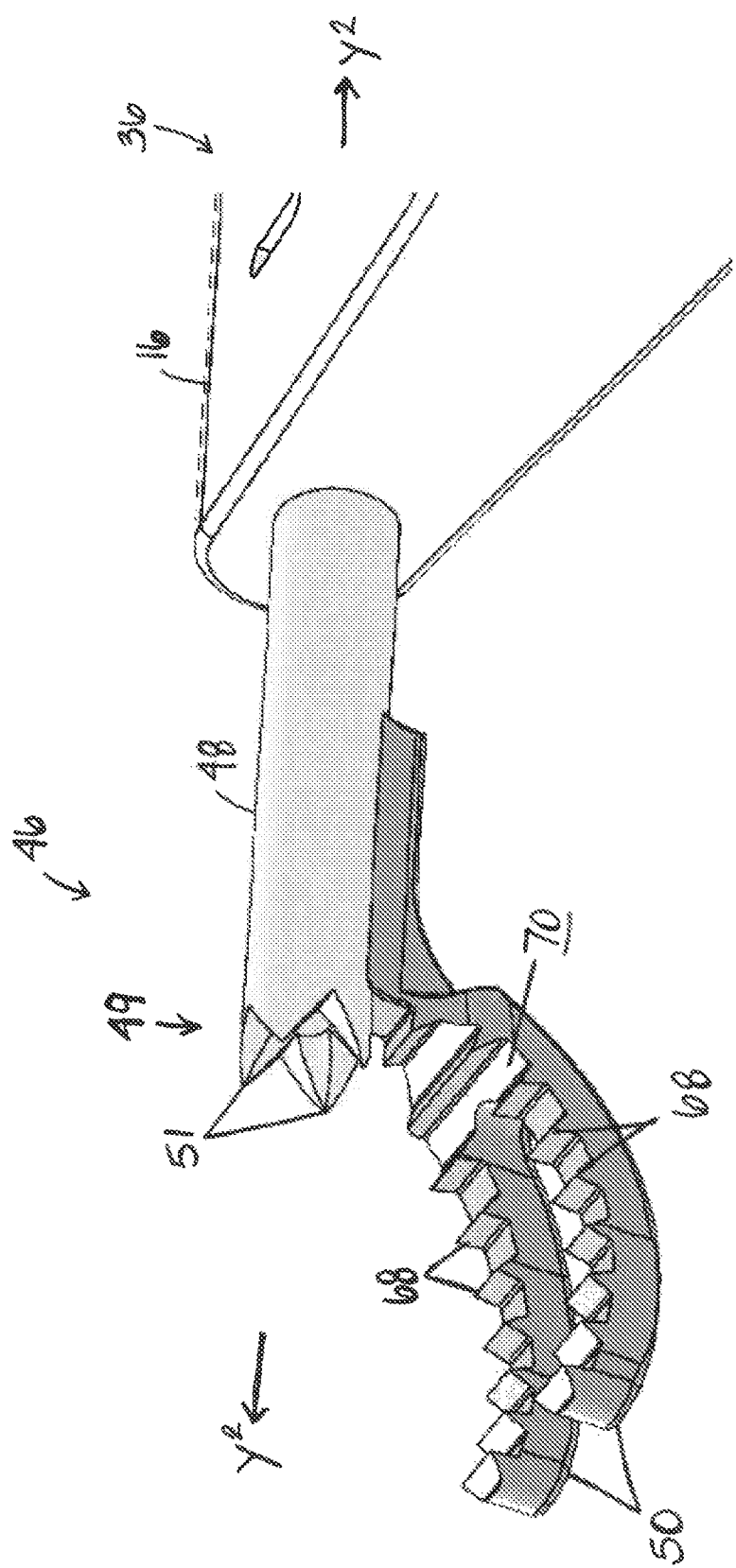
FIG. 5 is a close-up perspective view schematic representation of the drill bullet of the drill guide, according to an embodiment.
Figure 6:
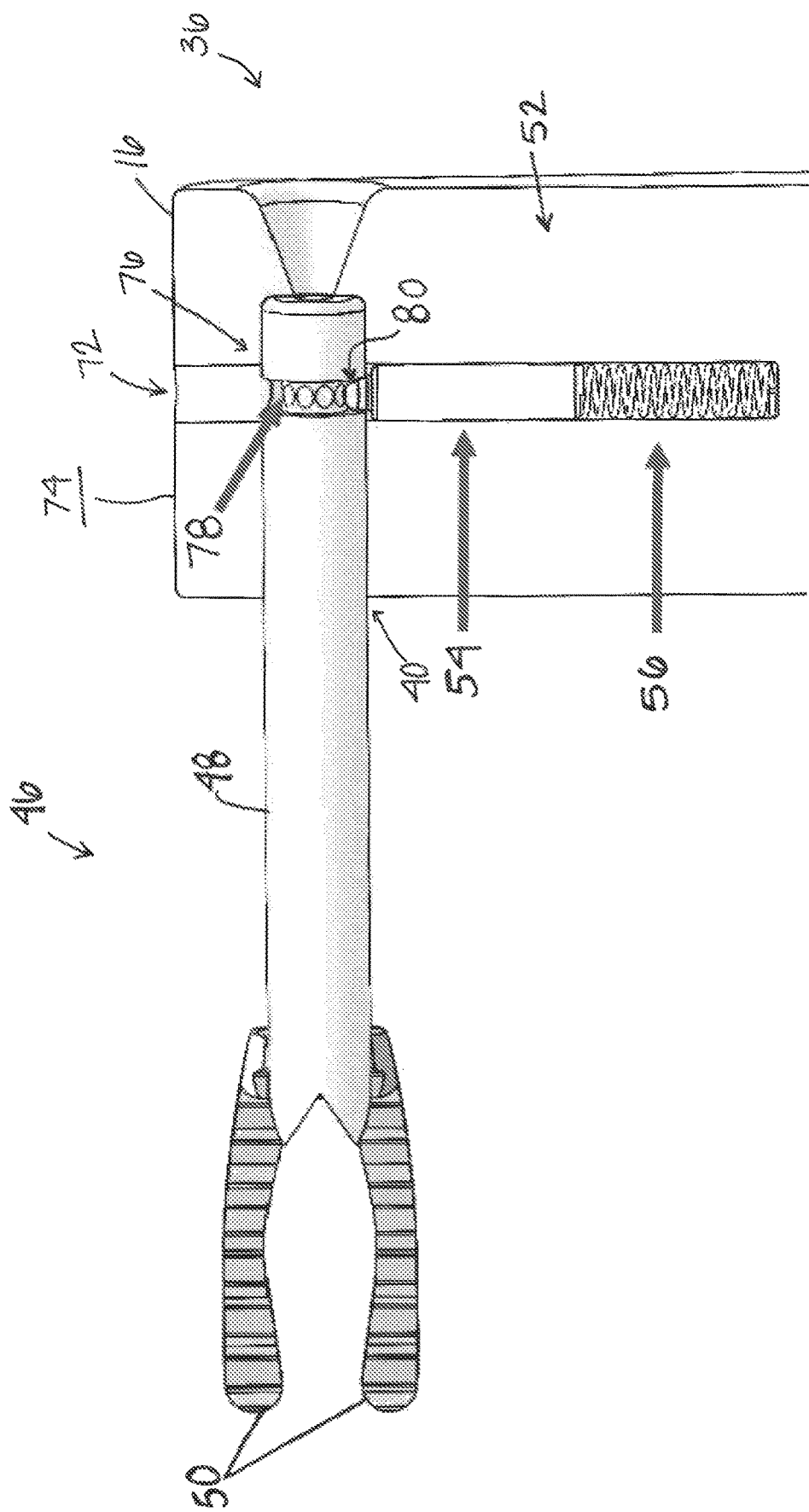
FIG. 6 is a close-up side view schematic representation of the drilling end of the guide body, according to an embodiment.

Referring now to FIGS. 5-6, there are shown various views schematic representation of the drilling end 36 of the guide body 16. FIG. 5 shows a close-up perspective view of the arms 50 of the drill bullet 46. As stated above, the pair of arms 50 can be connected to and extend from the shaft 48 of the drill bullet 46. In the depicted embodiment, the arms 50 are curved toward the central longitudinal y2-y2 axis in order to elevate the first metacarpal. The embodiment in FIG. 5 can also include a plurality of teeth 68 (or ridges) along an inner surface 70 of the arms 50. The base of the first metacarpal rests on the teeth 68 when the patient's hand is in the desired position within the drill guide 10. The arms 50 and the teeth 68 can be important for supporting and maintaining the position of the first metacarpal as the first metacarpal is typically loose in the joint after removal of the trapezium. A distal end 49 of the shaft 48 can also include a plurality of spaced, sharp tips 51 extending distally therefrom. The sharp tips 51 are used for additional support in maintaining the position of the first metacarpal.

FIG. 6 shows a close-up side view of the locking mechanism 52 of the drilling end 36 of the guide body 16. As shown in FIG. 6, a channel 72 extends through a surface 74 of the drilling end 36 and into the guide body 16. The spring 56 and the slug 54 are within the channel 72, with the slug 54 extending at least partially into the inner volume 40 of the drilling end 36 of the guide body 16. In the inner volume 40, the slug 54 engages the shaft 48 of the drill bullet 46. A proximal end 76 of the shaft 48 comprises a plurality of grooves 78. The grooves 78 extend circumferentially around the shaft 48.

Still referring to FIG. 6, a tip 80 of the slug 54 extends into one of the plurality of grooves 78 at a time. The spring 56 is biased to apply just enough force to maintain the tip 80 of the slug 54 in one of the plurality of grooves 78. The force applied by the spring 56 does not fully prevent rotation of the drill bullet 46 within the inner volume 40. In use, the surgeon can rotate the drill bullet 46 so that the arms 50 are in a desired position at the base of the thumb. The drill bullet 46 is automatically maintained in the desired position as the tip 80 of the slug 54 moves into another of the plurality of grooves 78 as the drill bullet 46 rotates. This saves time because there is no step that the surgeon needs to accomplish before he or she can rotate the drill bullet 46 and no step to lock it in place after the desired position is reached.

Figure 7:
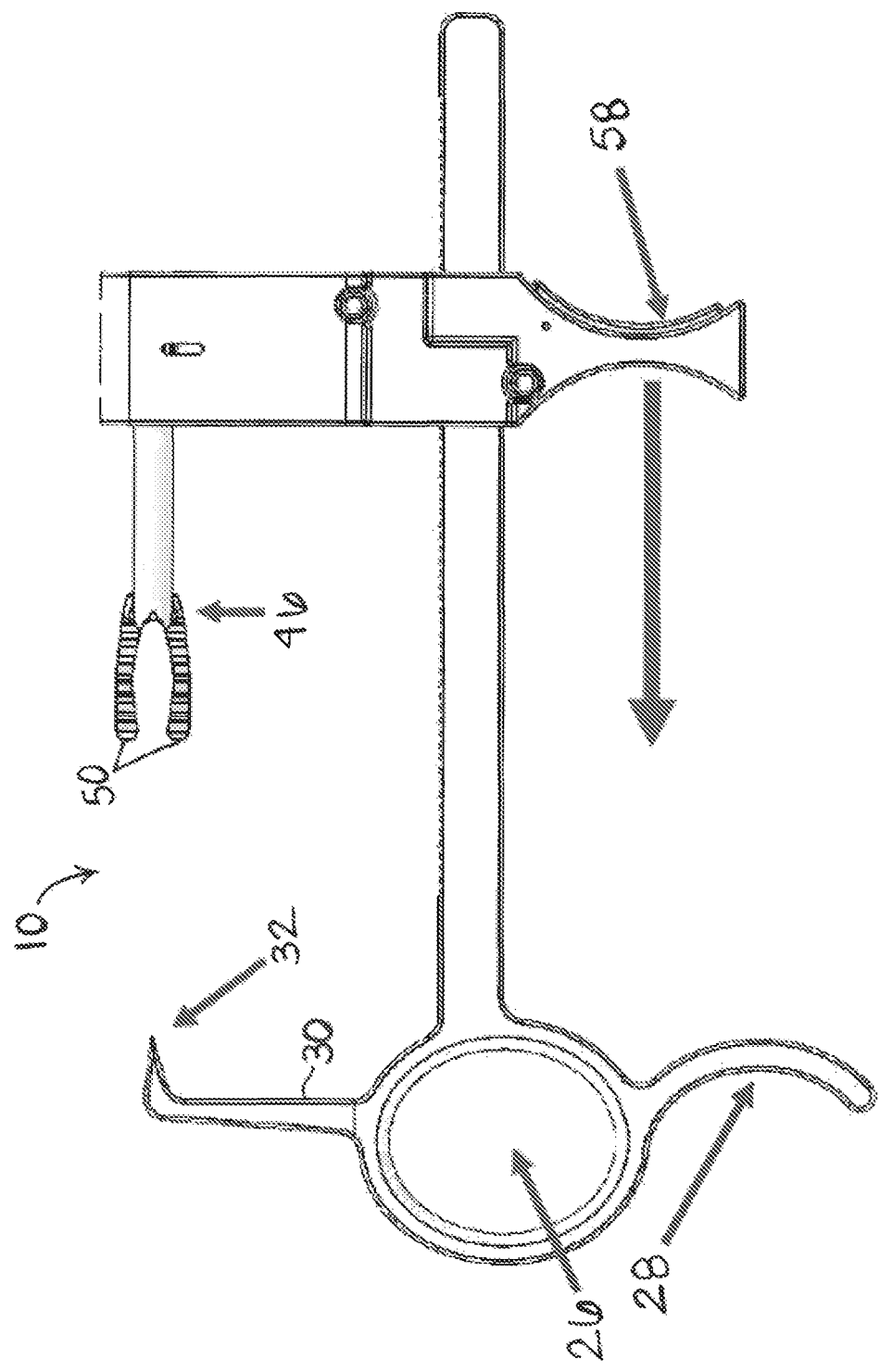
FIG. 7 is a side view schematic representation of the drill guide in the locked position, according to an embodiment.

Referring now to FIG. 7, there is shown a side view schematic representation of the drill guide 10 in the locked position, according to an embodiment. The drill guide 10 can be operated using one hand. The surgeon positions the sharp tip 32 of the spike 30 onto a desired drilling location on a second metacarpal (as should be understood by a person of ordinary skill in the art in conjunction with a review of this disclosure). Specifically, the sharp tip 32 is positioned on the bone where the surgeon would like the drill with drill bit (not shown) to exit from. Then, holding the drill guide 10 with his or her fingers on the ring 26 and the hook 28, and thumb on the trigger 58, the surgeon squeezes his or her hand to bring the arms 50 of the drill bullet 46 tight against the base of the patient's thumb (assuming the base of the thumb is the desired start location for the drill tunnel). Then, by releasing pressure on the trigger 58, the drill guide 10 will automatically lock in position and maintain the pressure that the surgeon applied.

Figure 8:
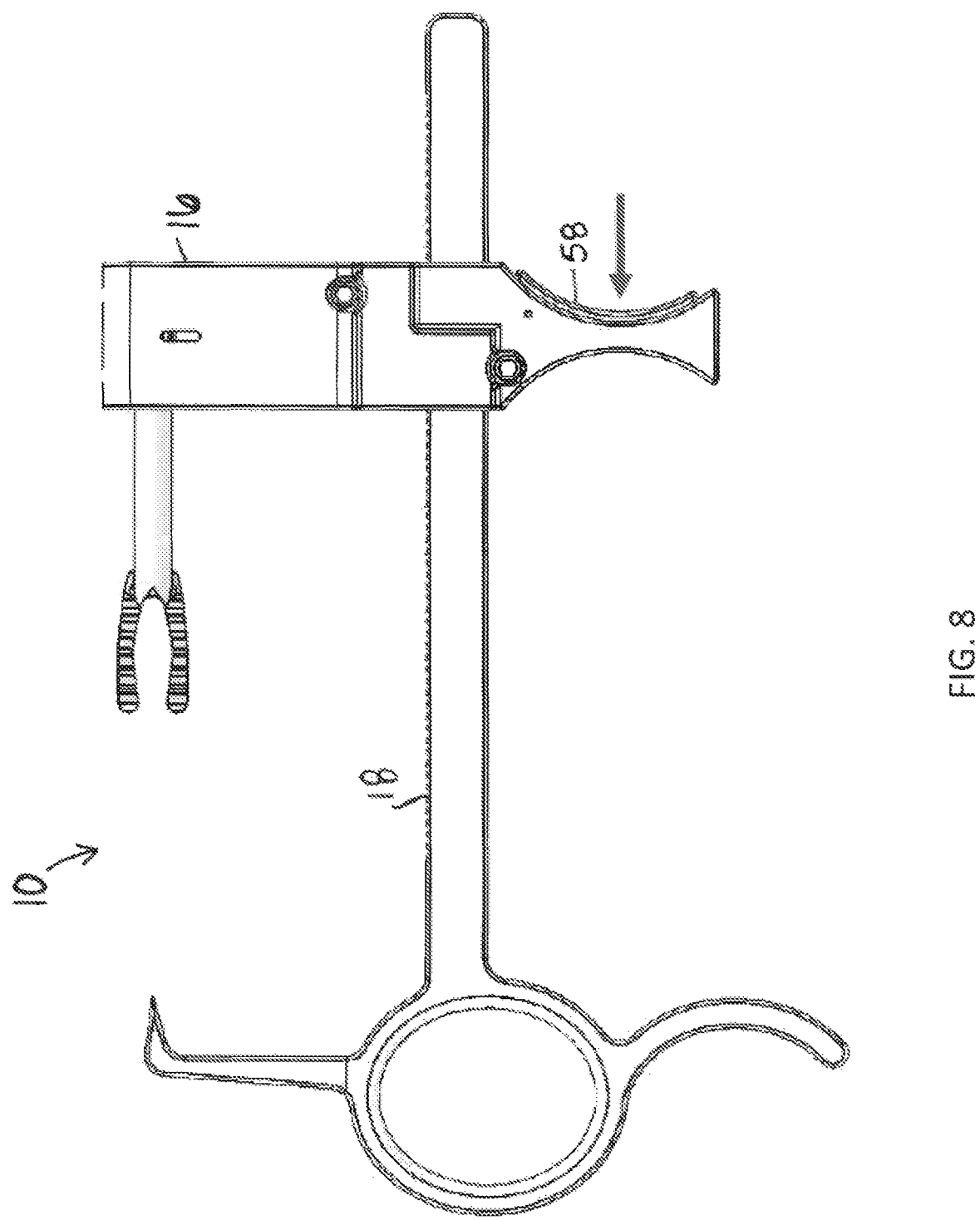
FIG. 8 is a side view schematic representation of the drill guide in the unlocked position, according to an embodiment.

Turning now to FIG. 8, there is shown a side view schematic representation of the drill guide 10 in the unlocked position, according to an embodiment. After drilling the tunnel through the first and second metacarpals, the drill guide 10 is removed by first, pinching the trigger 58, and second, pulling the sliding guide body 16 in the proximal direction away from the bone. Thereafter, while still pinching the trigger 58, the guide body 16 can be pulled off the guide rail 18. With the guide body 16 removed, the guide rail 18 can be easily removed from its position on the patient's hand.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A drill guide, comprising:
    a guide rail having an elongated shaft;
    a guide body with an aperture extending therethrough, the aperture configured to receive the elongated shaft of the guide rail;
    a trigger end of the guide body having a locking mechanism movable between an unlocked position and a locked position;
    wherein in the unlocked position, the guide body is slidable along the guide rail in a proximal direction; and
    wherein the drill guide further comprises:
        a distal ring connected to the elongated shaft and having an outer perimeter;
        a spike attached to a first position on the outer perimeter of the distal ring and extending therefrom; and
        a hook attached to a second position on the outer perimeter of the distal ring and extending therefrom such that the hook and the spike extend from opposing positions along the outer perimeter of the distal ring.

2. The drill guide of claim 1, wherein in the locked position, the guide body is only slidable along the guide rail in a distal direction.

3. The drill guide of claim 1, further comprising a trigger attached to the trigger end of the guide body, the trigger having the aperture of the guide body extending therethrough.

4. The drill guide of claim 3, further comprising a plurality of ridges on at least a portion of a surface of the guide rail.

5. The drill guide of claim 4, wherein in the locked position, the trigger catches at least one of the plurality of ridges when the guide body is pulled in the proximal direction.

6. The drill guide of claim 3, wherein the locking mechanism includes a spring, which is compressed by the trigger in the unlocked position.

7. A drill guide, comprising:
a guide rail having an elongated shaft;
a guide body with an aperture extending therethrough, the aperture configured to receive the elongated shaft of the guide rail;
a drilling end of the guide body with an aperture, creating an inner volume extending therethrough, the inner volume configured to receive a drill bullet therein;
wherein the drill bullet is rotatable within the inner volume of the drilling end of the guide body; and
wherein the drill guide further comprises:
a distal ring connected to the elongated shaft and having an outer perimeter;
a spike attached to a first position on the outer perimeter of the distal ring and extending therefrom; and
a hook attached to a second position on the outer perimeter of the distal ring and extending therefrom such that the hook and the spike extend from opposing positions along the outer perimeter of the distal ring.

8. The drill guide of claim 7, further comprising a plurality of grooves extending circumferentially around the drill bullet.

9. The drill guide of claim 8, further comprising a locking mechanism within the drilling end of the guide body configured to stop rotation of the drill bullet.

10. The drill guide of claim 9, wherein the locking mechanism includes a slug biased by a spring such that at least a portion of the slug is within one of the plurality of grooves.

11. The drill guide of claim 7, wherein the drill bullet comprises a shaft connected to a pair of arms extending in a distal direction.

12. The drill guide of claim 11, further comprising a plurality of teeth along an inner surface of at least one of the arms.

13. The drill guide of claim 7, wherein a distal end of the drill bullet comprises a plurality of spaced, sharp tips extending in a distal direction.

14. A drill guide, comprising:
a guide rail having an elongated shaft extending along a first central longitudinal axis;
a guide body with an aperture extending therethrough, the aperture configured to receive the elongated shaft of the guide rail;
a distal ring connected to the elongated shaft and having an outer perimeter;
a spike attached to a first position on the outer perimeter of the distal ring and extending therefrom; and
a hook attached to a second position on the outer perimeter of the distal ring and extending therefrom such that the hook and the spike extend from opposing positions along the outer perimeter of the distal ring.

15. The drill guide of claim 14, wherein the spike extends along a central lateral axis and the first central longitudinal axis is substantially perpendicular to the central lateral axis.

16. The drill guide of claim 15, wherein the ring is substantially planar with the central lateral axis.

17. The drill guide of claim 14, further comprising a sharp tip extending proximally from the spike.

18. The drill guide of claim 17, wherein the sharp tip extends along a second central longitudinal axis which is substantially parallel to the first central longitudinal axis.

19. The drill guide of claim 14, further comprising a trigger end of the guide body having a trigger, wherein the trigger, when actuated, allows the guide body to slide along the guide rail in a proximal direction.

20. The drill guide of claim 14, further comprising a drilling end of the guide body having a rotatable drill bullet extending distally therefrom, wherein the drill bullet is substantially aligned with the sharp tip of the spike.

* * * * *